(12) United States Patent
Dickerson et al.

(10) Patent No.: US 7,892,546 B2
(45) Date of Patent: Feb. 22, 2011

(54) ANTI-CXCR4 ANTIBODIES

(75) Inventors: Cindy Takeuchi Dickerson, San Diego, CA (US); David Matthew Marquis, Encinitas, CA (US); Victor H. Obungu, Fishers, IN (US); Sheng-Bin Peng, Carmel, IN (US); Peter Edward Vaillancourt, Del Mar, CA (US)

(73) Assignee: Eli Lilly and Company, Indianapolis, IN (US)

( * ) Notice: Subject to any disclaimer, the term of this patent is extended or adjusted under 35 U.S.C. 154(b) by 1 day.

(21) Appl. No.: 12/436,925

(22) Filed: May 7, 2009

(65) Prior Publication Data

US 2010/0285005 A1 Nov. 11, 2010

Related U.S. Application Data

(60) Provisional application No. 61/053,192, filed on May 14, 2008.

(51) Int. Cl.
*A61K 39/00* (2006.01)
*A61K 39/395* (2006.01)
*C07K 16/00* (2006.01)
*C12P 21/08* (2006.01)

(52) U.S. Cl. ............... 424/133.1; 424/139.1; 424/141.1; 424/143.1; 424/144.1; 530/387.1; 530/387.3; 530/387.9; 530/388.1; 530/388.15; 530/388.22

(58) Field of Classification Search ........................ None
See application file for complete search history.

(56) References Cited

U.S. PATENT DOCUMENTS

| | | | |
|---|---|---|---|
| 5,776,457 A | 7/1998 | Lee et al. | |
| 5,840,856 A | 11/1998 | Chuntharapai et al. | |
| 5,994,515 A * | 11/1999 | Hoxie .................... | 530/388.22 |
| 6,863,887 B1 | 3/2005 | Murphy et al. | |
| 6,949,243 B1 | 9/2005 | Mueller et al. | |
| 2004/0132642 A1 | 7/2004 | Hwang | |
| 2004/0209837 A1 * | 10/2004 | Kishimoto et al. ............ | 514/44 |
| 2007/0003558 A1 | 1/2007 | von Andrian et al. | |
| 2007/0059308 A1 | 3/2007 | Hua et al. | |
| 2010/0055088 A1 * | 3/2010 | Peled et al. ............... | 424/130.1 |

FOREIGN PATENT DOCUMENTS

| | | |
|---|---|---|
| WO | WO 92/17497 A1 | 10/1992 |
| WO | WO 99/48528 A1 | 9/1999 |
| WO | WO 99/50461 A1 | 10/1999 |
| WO | WO 01/38352 A2 | 5/2001 |
| WO | WO 03/066830 A2 | 8/2003 |
| WO | WO 2004/059285 A2 | 7/2004 |
| WO | WO 2004/074506 A2 | 9/2004 |
| WO | WO 2006/089141 A2 | 8/2006 |
| WO | WO 2008/060367 A2 | 5/2008 |

OTHER PUBLICATIONS

Paul, Fundamental Immunology, 3r~ Edition, 1993, pp. 292-295, under the heading "Fv Structure and Diversity in Three Dimensions".*
Rudikoff et al Proc. Natl. Acad. Sci.USA, 79(6):1979-1983, Mar. 1982.*
Colman P. M. Research in Immunology, 145:33-36, 1994.*
Carnec, X., et al., Journal of Virology, "*Anti-CXCR4 Monoclonal Antibodies Recognizing Overlapping Epitopes Differ Significantly in Their Ability to Inhibit Entry of Human Immunodeficiency Virus Type 1*", 79;3: 1930-1933 (2005).
Muller, A., et al., Nature, "*Involvement of chemokine receptors in breast cancer metastasis*", 410: 50-56 (2001).
Vermont-Desroches C., et al., Diaclone Technical Document, "*Evaluation of anti CXCR-4 Antibodies*", CR4.1.
Ghannadan, M., et al., International Archives of Allergy and Immunology, "*Detection of Novel CD Antigens on the Surface of Human Mast Cells and Basophils*", 127: 299-307 (2002).
Yang, H., et al., Immunology Letters, "*Antibody to CD14 like CXCR4-specific antibody 12G5 could inhibit CXCR4-dependent chemotaxis and HIV Env-mediated cell fusion*", 88: 27-30 (2003).

* cited by examiner

*Primary Examiner*—Shulamith H. Shafer
(74) *Attorney, Agent, or Firm*—Andrea M. Castetter

(57) ABSTRACT

The present invention provides antibodies that bind human CXCR4 and are characterized as having high affinity and strong neutralizing properties. The antibodies of the invention are useful in the treatment of tumorigenesis, including tumor growth, invasion, angiogenesis, or metastasis.

10 Claims, No Drawings

ANTI-CXCR4 ANTIBODIES

This application claims the priority of U.S. provisional application No. 61/053,192, filed May 14, 2008.

The present invention relates to monoclonal antibodies against CXCR4 and their use in treating diseases in which pathogenesis is mediated by CXCR4 and SDF-1.

CXCR4, a chemokine receptor, is a G protein-coupled, seven-transmembrane receptor. Like other chemokine receptors, CXCR4 plays an important role in immune and inflammatory responses by mediating the directional migration and activation of leukocytes. CXCR4 is expressed or overexpressed in a variety of cancer cell lines and tissues including breast, prostate, lung, ovarian, colon, pancreatic, kidney, and brain, as well as non-Hodgkin's lymphoma and chronic lymphocytic leukemia. The only known ligand to CXCR4 is stromal cell-derived factor-1 (SDF-1, or CXCL12). The CXCR4 and SDF-1 interaction plays an important role in multiple phases of tumorigenesis, including tumor growth, invasion, angiogenesis, and metastasis.

In view of the involvement of CXCR4 in various serious diseases, CXCR4 has been studied as a therapeutic target. For example, AMD3100, a bicyclam CXCR4 antagonist, is available for patients with multiple myeloma and non-Hodgkins lymphoma. CTCE9908, a peptide CXCR4 antagonist, is currently in Phase Ib/II clinical trials for cancer. In addition, antibodies targeting CXCR4 are disclosed in the art (WO 06/089141, US 07/0059308, and in Carnec et al [Carnec X, Quan L, Olson W, Hazan U, Dragic T. (2005) Anti-CXCR4 Monoclonal Antibodies Recognizing Overlapping Epitopes Differ Significantly in Their Ability To Inhibit Entry of Human Immunodeficiency Virus Type I. Journal of Virology. February 2005: 1930-1933]).

Although there are various agents under development that target CXCR4, there still exists a need for additional therapeutic agents targeting CXCR4. The antibodies of the present invention are therapeutically useful CXCR4 antagonists possessing a number of desirable properties. Antibodies of the present invention have increased chemical and physical stability, and solubility. The present invention provides CXCR4 antibodies that bind human CXCR4 with high affinity and inhibit human CXCR4 binding to SDF-1. High potency permits the use of low doses in therapeutic regimens. In addition, these antibodies interfere with the interaction of SDF-1 to CXCR4, and thus reduce tumorigenesis, including tumor growth, invasion, angiogenesis, and metastasis. Furthermore, antibodies of the present invention induce apoptosis of tumor cells.

The present invention includes a human engineered antibody or a binding fragment thereof, that binds human CXCR4, and which:
a. inhibits binding of human SDF-1α (SEQ ID NO:33) to CXCR4 with an $IC_{50}$ for human CXCR4 between 10 nM and 0.05 nM in a human CXCR4/$^{125}$I-SDF-1α binding inhibition assay as described herein;
b. inhibits migration of cells bearing CXCR4 on their surface with an $IC_{50}$ between 30 nM and 0.3 nM in the chemotaxis assay as described herein; and
c. exhibits an affinity, $K_D$ between 15 nM and 0.05 nM in the Surface Plasmon Reasonance (BIAcore) assay as described herein.

The present invention preferably provides a human engineered antibody or a binding fragment thereof, that binds human CXCR4, and which inhibits binding of human SDF-1α (SEQ ID NO:33) to CXCR4 with an $IC_{50}$ for human CXCR4 between 0.5 nM and 0.05 nM in a human CXCR4/$^{125}$I-SDF-1α binding inhibition assay as described herein.

The present invention preferably provides a human engineered antibody or a binding fragment thereof, that binds human CXCR4, and which inhibits migration of cells bearing CXCR4 on their surface with an $IC_{50}$ between 3.0 nM and 0.3 nM in the chemotaxis assay as described herein.

The present invention preferably provides a human engineered antibody or a binding fragment thereof, that binds human CXCR4, and which exhibits an affinity, $K_D$ between 1.0 nM and 0.05 nM in the Surface Plasmon Reasonance (BIAcore) assay as described herein.

The present invention preferably provides a human engineered antibody or a binding fragment thereof, that binds human CXCR4, and which exhibits anti-tumorigenesis activity by preventing tumor growth in a tumor xenograft model as described herein when administered at 1 mg/kg.

The present invention preferably provides a human engineered antibody or a binding fragment thereof, that binds human CXCR4, and which induces apoptosis of tumor cells in an apoptosis assay as described herein when administered between 2 µg/mL and 10 µg/mL.

The present invention includes a human engineered antibody or a binding fragment thereof, that comprises a light chain comprising a light chain variable region that comprises framework regions, CDRL1 having the amino acid sequence of SEQ ID NO:8, CDRL2 having the amino acid sequence of SEQ ID NO:9, and CDRL3 having the amino acid sequence of SEQ ID NO:10, and a heavy chain comprising a heavy chain variable region that comprises framework regions, CDRH1 having the amino acid sequence of SEQ ID NO:1, CDRH3 having the amino acid sequence of SEQ ID NO:3, and CDRH2 having an amino sequence selected from the group consisting of SEQ ID NO:2, SEQ ID NO:4, SEQ ID NO:5, SEQ ID NO:6, and SEQ ID NO:7, wherein the antibody binds to human CXCR4.

Further, the present invention includes an antibody that binds human CXCR4, wherein a light chain comprises an amino acid sequence of SEQ ID NO:16, and a heavy chain comprises an amino acid sequence selected from the group consisting of SEQ ID NO:11, SEQ ID NO:12, SEQ ID NO:13, SEQ ID NO:14, and SEQ ID NO:15.

In addition, the present invention includes an antibody that binds human CXCR4, wherein a light chain comprises an amino acid sequence of SEQ ID NO:22, and a heavy chain comprises an amino acid sequence selected from the group consisting of SEQ ID NO:17, SEQ ID NO:18, SEQ ID NO:19, SEQ ID NO:20, and SEQ ID NO:21.

The present invention also includes an antibody that binds human CXCR4, wherein an antibody is selected from the group consisting of an antibody comprising SEQ ID NO:17 and SEQ ID NO:22, an antibody comprising SEQ ID NO:18 and SEQ ID NO:22, an antibody comprising SEQ ID NO:19 and SEQ ID NO:22, an antibody comprising SEQ ID NO:20 and SEQ ID NO:22, and an antibody comprising SEQ ID NO:21 and SEQ ID NO:22.

The antibodies of the present invention as defined herein are characterized by having an $IC_{50}$ of 10 nM or less in a human CXCR4/$^{125}$I-SDF-1α binding inhibition assay as described herein. Preferred antibodies of the invention have a binding affinity for human CXCR4 of 5.0 nM or less. Most preferred antibodies of the invention have a binding affinity for human CXCR4 of 0.5 nM or less. Further preferred, antibodies of the present invention have an $IC_{50}$ for human CXCR4 between 10 nM and 0.05 nM in a human CXCR4/$^{125}$I-SDF-1α binding inhibition assay as described herein. Further preferred, antibodies of the present invention have an $IC_{50}$ for human CXCR4 between 0.5 nM and 0.05 nM in a human $CXCR4/^{125}I$-SDF-1α binding inhibition assay as described herein.

The antibodies of the present invention as defined herein are characterized by having an $IC_{50}$ of 30 nM or less in a chemotaxis assay as described herein. Preferred antibodies of the invention have an $IC_{50}$ of 15 nM or less in the chemotaxis assay. More preferred antibodies of the invention have an $IC_{50}$ of 3.0 nM or less in the chemotaxis assay. Further preferred, antibodies of the present invention have an $IC_{50}$ between 30 nM and 0.3 nM in the chemotaxis assay as described herein. Further preferred, antibodies of the present invention have an $IC_{50}$ between 3.0 nM and 0.3 nM in the chemotaxis assay as described herein.

The antibodies of the present invention as defined herein are characterized by having a $K_D$ of 15 nM or less in an assay that evaluates the binding activities of the antibodies by Surface Plasmon Reasonance (BIAcore) as described herein. More preferred antibodies of the invention $K_D$ of 10 nM or less in the BIAcore assay. Most preferred antibodies of the invention have $K_D$ of 1.0 nM or less in the BIAcore assay. Further preferred, antibodies of the present invention have $K_D$ between 15 nM and 0.05 nM in the BIAcore assay as described herein. Further preferred, antibodies of the present invention have $K_D$ between 1.0 nM and 0.05 nM in the BIAcore assay as described herein.

The antibodies of the present invention as defined herein are characterized by having anti-tumorigenesis activity by preventing tumor growth in a tumor xenograft model using NOD/SCID mice and human non-Hodgkin's lymphoma Namalwa cells as described herein when administered at 10 mg/kg. More preferred antibodies of the invention have having anti-tumorigenesis activity by preventing tumor growth when administered at 1 mg/kg.

The antibodies of the present invention as defined herein are characterized by inducing apoptosis of tumor cells in an apoptosis assay as described herein. More preferred antibodies of the invention induce nuclear fragmentation and activation of caspase 3, hallmarks of apoptosis, in multiple tumor cells including Namalwa and CEM cells when administered between 2 µg/mL and 10 µg/mL.

The present invention includes a pharmaceutical composition comprising an antibody as described herein in combination with one or more pharmaceutically acceptable carriers, diluents, or excipients. In addition, the present invention includes a pharmaceutical composition for the treatment of tumorigenesis, including tumor growth, invasion, angiogenesis, or metastasis, comprising an antibody as variously described herein, in combination with one or more pharmaceutically acceptable carriers, diluents, or excipients. Further, the present invention includes a pharmaceutical composition for the treatment of a cancer selected from the group consisting of breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and leukemia comprising an antibody as variously described herein, in combination with one or more pharmaceutically acceptable carriers, diluents, or excipients.

The present invention includes the use of an antibody as described herein for the preparation of a medicament for the treatment of tumorigenesis, including tumor growth, invasion, angiogenesis, or metastasis. In addition, the present invention includes the use of an antibody as described herein for the preparation of a medicament for the treatment of a cancer selected from the group consisting of breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and leukemia.

The present invention includes a method of treating tumorigenesis, including tumor growth, invasion, angiogenesis, or metastasis, comprising administering to a patient in need of an antibody as described herein. Further, the present invention includes a method of treating a cancer selected from the group consisting of breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and leukemia, comprising administering to a patient in need of an antibody as described herein.

The general structure of an "antibody," is very well-known in the art. For an antibody of the IgG type, there are four amino acid chains (two "heavy" chains and two "light" chains) that are cross-linked via intra- and inter-chain disulfide bonds. When expressed in certain biological systems, antibodies having unmodified human Fc sequences are glycosylated in the Fc region. Antibodies may be glycosylated at other positions as well. The subunit structures and three-dimensional configurations of antibodies are well known in the art. Each heavy chain is comprised of an N-terminal heavy chain variable region ("HCVR") and a heavy chain constant region ("HCCR"). The heavy chain constant region is comprised of three domains (CH1, CH2, and CH3) for IgG, IgD, and IgA; and 4 domains (CH1, CH2, CH3, and CH4) for IgM and IgE. Each light chain is comprised of a light chain variable region (herein "LCVR") and a light chain constant region ("LCCR").

The variable regions of each light/heavy chain pair form the antibody binding site. The HCVR and LCVR regions can be further subdivided into regions of hypervariability, termed complementarity determining regions (CDRs), interspersed with regions that are more conserved, termed framework regions (FR). Each HCVR and LCVR are composed of three CDRs and four FRs, arranged from amino-terminus to carboxy-terminus in the following order: FR1, CDR1, FR2, CDR2, FR3, CDR3, FR4. Herein, the 3 CDRs of the heavy chain are referred to as "CDRH1, CDRH2, and CDRH3" and the 3 CDRs of the light chain are referred to as "CDRL1, CDRL2 and CDRL3." The CDRs contain most of the residues which form specific interactions with the antigen. The assignment of amino acids to each domain is in accordance with well-known conventions [e.g., Kabat, "Sequences of Proteins of Immunological Interest," National Institutes of Health, Bethesda, Md. (1991)].

Antibodies of the present invention may have a heavy chain constant region selected from any of the immunoglobulin classes (IgA, IgD, IgG, IgM, and IgE). Furthermore, antibodies of the present invention contain an Fc portion which is derived from human IgG4 Fc region because of its reduced ability to bind complement factors as compared to other IgG sub-types.

An antibody may be derived from a single copy or clone, including e.g., any eukaryotic, prokaryotic, or phage clone. Preferably an antibody of the invention exists in a homogeneous or substantially homogeneous population. An antibody can be intact, comprising complete or full length constant regions, including the Fc region, or a portion or fragment of such an antibody provided that any shortened form comprises the antigen-binding portion and retains antigen-binding capability. Such shortened forms include, e.g., a Fab fragment, Fab' fragment or F(ab') 2 fragment that includes the CDRs or the variable regions of the anti-CXCR4 antibodies disclosed. Furthermore, such shortened antibody forms can be a single chain Fv fragment that may be produced by joining the DNA encoding the LCVR and HCVR with a linker sequence. (See, Pluckthun, The Pharmacology of Monoclonal Antibodies, vol. 113, Rosenburg and Moore eds., Springer-Verlag, New York, pp 269-315, 1994). Regardless of whether fragments or portions are specified, the term "antibody" as used herein includes such fragments or portions as well as single chain forms unless otherwise indicated. As long as the protein retains the ability to specifically or preferentially bind CXCR4 and includes a sequence or sequences disclosed herein, it is included within the term "antibody." Antibodies of the invention can be produced using techniques well known in the art, e.g., recombinant technologies, phage display technologies, synthetic technologies or combinations of such technologies or other technologies readily known in the art.

The term "human engineered antibody" refers to an antibody having frameworks, hinge regions, and constant regions of human origin that are identical with or substantially identical (substantially human) with frameworks and constant regions derived from human genomic sequences. Fully human frameworks, hinge regions, and constant regions are those human germline sequences as well as sequences with naturally-occurring somatic mutations. A human engineered antibody may comprise framework, hinge, or constant regions derived from a fully human framework, hinge, or constant region containing one or more amino acid substitutions, deletions, or additions therein. Often, a human engineered antibody is preferably substantially non-immunogenic in humans.

A variety of different human framework sequences may be used singly or in combination as a basis for the human engineered antibodies of the present invention. Preferably, the framework regions of the antibodies of the invention are of human origin or substantially human (at least 95%, 97% or 99% of human origin.) The sequences of framework regions of human origin may be obtained from The Immunoglobulin Factsbook, by Marie-Paule Lafranc, Gerard Lefranc, Academic Press 2001, ISBN 012441351.

The framework sequence for the human engineered antibodies of the present invention serves as the "donor" variable framework region and can be used to create additional human engineered antibodies with the same CDRs specified herein using methodology known in the art. Furthermore, the framework sequence for the human engineered antibodies of the present invention can be compared to other known human framework sequences to generate additional human engineered antibodies. Thus, this information can be used to "back-mutate" another selected homologous human framework region to the human engineered donor amino acid residue at these positions. Further, any "rare" amino acids can be detected in additional human frameworks such that the concensus or donor human engineered amino acid residue can be used at the relevant position.

The term "inhibit" means the ability to substantially antagonize, prohibit, prevent, restrain, slow, disrupt, eliminate, stop, reduce or reverse the biological effects of binding to the CXCR4 receptor.

"CXCR4" or "human CXCR4" refers to any human CXCR4, as well as functionally active, mutated forms thereof Examples include, but are not limited to, SEQ ID NO:30, SEQ ID NO:31, and SEQ ID NO:32.

A "patient" is a mammal, preferably a human.

The term "treating" (or "treat" or "treatment") means slowing, stopping, reducing, or reversing the progression or severity of a symptom, disorder, condition, or disease.

The term "preventing" (or "prevent" or "prevention") means prohibiting, restraining, or inhibiting the incidence or occurrence of a symptom, disorder, condition, or disease. Acute events and chronic conditions may be treated and prevented. In an acute event, antibody is administered at the onset of a symptom, disorder, condition, or disease and discontinued when the acute event ends, whereas a chronic symptom, disorder, condition, or disease is treated over a more protracted time frame.

The term "therapeutically effective amount" refers to the amount or dose of an antibody of this invention which, upon single or multiple dose administration to a patient, provides the desired treatment or prevention. The therapeutically effective amount can comprise an amount of about 0.001 to 20 mg/kg per single (e.g., bolus), multiple or continuous administration.

Particular antibodies of this invention include: an antibody comprising amino acid sequences of SEQ ID NOs: 1, 2, 3, 8, 9, and 10; an antibody comprising amino acid sequences of SEQ ID NOs: 1, 4, 3, 8, 9, and 10; an antibody comprising amino acid sequences of SEQ ID NOs: 1, 5, 3, 8, 9, and 10; an antibody comprising amino acid sequences of SEQ ID NOs: 1, 6, 3, 8, 9, and 10; an antibody comprising amino acid sequences of SEQ ID NOs: 1, 7, 3, 8, 9, and 10. The listed sequences represent CDRH1, CDRH2, CDRH3, CDRL1, CDRL2, and CDRL3, respectively.

Particular antibodies of this invention include: an antibody comprising a LCVR having an amino acid sequence of SEQ ID NO: 16 and a HCVR having an amino acid sequence of SEQ ID NO: 11; an antibody comprising a LCVR having an amino acid sequence of SEQ ID NO: 16 and a HCVR having an amino acid sequence of SEQ ID NO:12; an antibody comprising a LCVR having an amino acid sequence of SEQ ID NO: 16 and a HCVR having an amino acid sequence of SEQ ID NO:13; an antibody comprising a LCVR having an amino acid sequence of SEQ ID NO: 16 and a HCVR having an amino acid sequence of SEQ ID NO:14; an antibody comprising a LCVR having an amino acid sequence of SEQ ID NO: 16 and a HCVR having an amino acid sequence of SEQ ID NO:15.

The present invention includes five antibodies that bind and inhibit CXCR4 activity. In particular, the present invention includes: an antibody comprising a light chain having an amino acid sequence of SEQ ID NO: 22 and a heavy chain having an amino acid sequence of SEQ ID NO: 17; an antibody comprising a light chain having an amino acid sequence of SEQ ID NO: 22 and a heavy chain having an amino acid sequence of SEQ ID NO: 18; an antibody comprising a light chain having an amino acid sequence of SEQ ID NO: 22 and a heavy chain having an amino acid sequence of SEQ ID NO: 19; an antibody comprising a light chain having an amino acid sequence of SEQ ID NO: 22 and a heavy chain having an amino acid sequence of SEQ ID NO: 20; an antibody comprising a light chain having an amino acid sequence of SEQ ID NO: 22 and a heavy chain having an amino acid sequence of SEQ ID NO: 21.

Preferably, an antibody of the present invention wherein all six CDRs, the HCVR, the LCVR, the HCVR and the LCVR, the entire heavy chain, the entire light chain, or the entire heavy chain and light chain are limited by a particular sequence as shown by a SEQ ID NO: herein is further characterized by having an $IC_{50}$ in a human CXCR4/$^{125}$I-SDF-1$\alpha$ binding inhibition assay as described herein of about of 10 nM or less, more preferably about 5.0 nM or less, and most preferably of 0.5 nM or less. Further preferred, an antibody of the present invention wherein all six CDRs, the HCVR, the LCVR, the HCVR and the LCVR, the entire heavy chain, the entire light chain, or the entire heavy chain and light chain are limited by a particular sequence as shown by a SEQ ID NO: herein is further characterized by having an $IC_{50}$ for human CXCR4 between 10 nM and 0.05 nM in a human CXCR4/$^{125}$I-SDF-1α binding inhibition assay as described herein. Further preferred, an antibody of the present invention wherein all six CDRs, the HCVR, the LCVR, the HCVR and the LCVR, the entire heavy chain, the entire light chain, or the entire heavy chain and light chain are limited by a particular sequence as shown by a SEQ ID NO: herein is further characterized by having an $IC_{50}$ for human CXCR4 between 0.5 nM and 0.05 nM in a human CXCR4/$^{125}$I-SDF-1α binding inhibition assay as described herein.

More preferably, an antibody of the present invention wherein all six CDRs, the HCVR, the LCVR, the HCVR and the LCVR, the entire heavy chain, the entire light chain, or the entire heavy chain and light chain are limited by a particular sequence as shown by a SEQ ID NO: herein is further characterized by having an $IC_{50}$ in a chemotaxis assay as described herein of about 30 nM or less, more preferably about 15 nM or less, and even more preferably 3.0 nM or less. Further preferred, an antibody of the present invention wherein all six CDRs, the HCVR, the LCVR, the HCVR and the LCVR, the entire heavy chain, the entire light chain, or the entire heavy chain and light chain are limited by a particular sequence as shown by a SEQ ID NO: herein is further characterized by having an $IC_{50}$ between 30 nM and 0.3 nM in the chemotaxis assay as described herein. Further preferred, an antibody of the present invention wherein all six CDRs, the HCVR, the LCVR, the HCVR and the LCVR, the entire heavy chain, the entire light chain, or the entire heavy chain and light chain are limited by a particular sequence as shown by a SEQ ID NO: herein is further characterized by having an $IC_{50}$ between 3.0 nM and 0.3 nM in the chemotaxis assay as described herein.

Even more preferably, an antibody of the present invention wherein all six CDRs, the HCVR, the LCVR, the HCVR and the LCVR, the entire heavy chain, the entire light chain, or the entire heavy chain and light chain are limited by a particular sequence as shown by a SEQ ID NO: herein is further characterized by having a $K_D$ in an assay that evaluates the binding activities of the antibodies by Surface Plasmon Reasonance (BIAcore) as described herein of about 15 nM or less, more preferably about 10 nM or less, and most preferably 1.0 nM or less. Further preferred, an antibody of the present invention wherein all six CDRs, the HCVR, the LCVR, the HCVR and the LCVR, the entire heavy chain, the entire light chain, or the entire heavy chain and light chain are limited by a particular sequence as shown by a SEQ ID NO: herein is further characterized by having a $K_D$ in an assay that evaluates the binding activities of the antibodies by Surface Plasmon Resonance (BIAcore) as described herein between 15 nM and 0.05 nM in the BIAcore assay as described herein. Further preferred, an antibody of the present invention wherein all six CDRs, the HCVR, the LCVR, the HCVR and the LCVR, the entire heavy chain, the entire light chain, or the entire heavy chain and light chain are limited by a particular sequence as shown by a SEQ ID NO: herein is further characterized by having a $K_D$ in an assay that evaluates the binding activities of the antibodies by Surface Plasmon Reasonance (BIAcore) as described herein between 1.0 nM and 0.05 nM in the BIAcore assay as described herein.

More preferably, an antibody of the present invention wherein all six CDRs, the HCVR, the LCVR, the HCVR and the LCVR, the entire heavy chain, the entire light chain, or the entire heavy chain and light chain are limited by a particular sequence as shown by a SEQ ID NO: herein is further characterized by having anti-tumorigenesis activity by preventing tumor growth in a tumor xenograft model using NOD/SCID mice and human non-Hodgkin's lymphoma Namalwa cells as described herein when administered at 10 mg/kg, and even more preferably when administered at 1 mg/kg.

Most preferably, an antibody of the present invention wherein all six CDRs, the HCVR, the LCVR, the HCVR and the LCVR, the entire heavy chain, the entire light chain, or the entire heavy chain and light chain are limited by a particular sequence as shown by a SEQ ID NO: herein is further characterized by inducing apoptosis of tumor cells in an apoptosis assay as described herein. More preferred, an antibody of the present invention wherein all six CDRs, the HCVR, the LCVR, the HCVR and the LCVR, the entire heavy chain, the entire light chain, or the entire heavy chain and light chain are limited by a particular sequence as shown by a SEQ ID NO: herein is further characterized by inducing nuclear fragmentation and activation of caspase 3, hallmarks of apoptosis, in multiple tumor cells including Namalwa and CEM cells when administered between 2 μg/mL and 10 μg/mL.

EXAMPLES

Antibodies I, II, III, IV, and V can be made and purified as follows. An appropriate host cell, such as HEK 293 EBNA or CHO, is either transiently or stably transfected with an expression system for secreting antibodies using an optimal predetermined HC:LC vector ratio or a single vector system encoding both HC, such as SEQ ID NO: 23, SEQ ID NO: 24, SEQ ID NO: 25, SEQ ID NO: 26, or SEQ ID NO: 27 and LC, such as SEQ ID NO: 28. Clarified media, into which the antibody has been secreted, is purified using any of many commonly-used techniques. For example, the medium may be conveniently applied to a Protein A or G Sepharose FF column that has been equilibrated with a compatible buffer, such as phosphate buffered saline (pH 7.4). The column is washed to remove nonspecific binding components. The bound antibody is eluted, for example, by pH gradient (such as 0.1 M sodium phosphate buffer pH 6.8 to 0.1 M sodium citrate buffer pH 2.5). Antibody fractions are detected, such as by SDS-PAGE, and then are pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, or hydroxyapatite chromatography. The purity of the antibody after these chromatography steps is greater than 99%. The product may be immediately frozen at −70° C. or may be lyophilized. The amino acid sequences for these antibodies are provided below.

| | SEQ ID NOs | | | |
|---|---|---|---|---|
| Antibody | Heavy Chain | Light Chain | HCVR | LCVR |
| I | 17 | 22 | 11 | 16 |
| II | 18 | 22 | 12 | 16 |
| III | 19 | 22 | 13 | 16 |
| IV | 20 | 22 | 14 | 16 |
| V | 21 | 22 | 15 | 16 |

| Antibody | HCDR1 | HCDR2 | HCDR3 | LCDR1 | LCDR2 | LCDR3 |
|---|---|---|---|---|---|---|
| I | 1 | 2 | 3 | 8 | 9 | 10 |
| II | 1 | 4 | 3 | 8 | 9 | 10 |

-continued

| SEQ ID NOs | | | | | | |
|---|---|---|---|---|---|---|
| III | 1 | 5 | 3 | 8 | 9 | 10 |
| IV | 1 | 6 | 3 | 8 | 9 | 10 |
| V | 1 | 7 | 3 | 8 | 9 | 10 |

Human CXCR4/$^{125}$I-SDF-1α Binding Inhibition Assay

SDF-1 binding to CXCR4 is the first step in activating the CXCR4 intracellular signaling pathway. To determine if an antibody can block the interaction of SDF-1 and CXCR4, human leukemia CCRF-CEM cells expressing endogenous CXCR4 are used in an $^{125}$I-labeled SDF-1α binding assay. The assay is performed in a 96-well U-bottom, non-treated polystyrene plate. The binding assay buffer is prepared with RPMI 1640 medium containing 10 mM N-2-hydroxyethylpiperazine-N'-2-ethanesulfonic acid (HEPES), pH 7.5, and 0.2% bovine serum albumin (BSA). Briefly, 200 µL reaction mixtures containing 300 pM ligand (60 pM $^{125}$I-SDF-1α and 240 pM cold SDF-1α), different concentrations of the test antibody in assay buffer, 100,000 human CCRF-CEM cells, and 0.5 mg scintillation proximity assay (SPA) beads are incubated at room temperature for 2 hours. Plates are then counted in a liquid scintillation and luminescence counter in SPA mode. CXCR4 antagonists decrease the bound radioactivity in this assay in a dose-dependent manner. The inhibitory potency ($IC_{50}$) of a test antibody is calculated using GraphPad Prism software, based on the dose-dependent decrease of bound radioactivity.

Antibodies exemplified herein exhibit an $IC_{50}$ value of 10 nM or less in this assay. For example, the antibody III exhibits an average IC50 of 0.45 nM in this assay. The data demonstrate that antibodies exemplified herein bind to human CXCR4 with high affinity and inhibit human CXCR4 binding to SDF-1.

Chemotaxis Assay

CXCR4/SDF-1 interaction regulates migration (chemotaxis) of cells bearing CXCR4 on their surface. To determine the antagonist and cellular activities of a test antibody, a chemotaxis assay using human histiocytic lymphoma U937 cells that express endogenous CXCR4 is employed. Briefly, U937 cells, grown in Dulbecco's Modified Eagle Medium (D-MEM) containing 10% fetal bovine serum, 1% Minimum Essential Medium (MEM) sodium pyruvate solution, 1% MEM nonessential amino acids, and 1% L-glutamine, are harvested and washed once with chemotaxis assay buffer (1×RPMI medium containing 10 mM HEPES, pH 7.5, and 0.3% BSA.) After washing, cells are resuspended in assay buffer at a concentration of 5×10$^6$ cells/mL. The assay is performed in a 96-well cell migration plate. Generally, 50 µL of cell mixture with or without test antibody, ranging from 0.5 µg/mL to 50 µg/mL, is plated on the upper chamber, and 30 µL of SDF-1α (10 ng/mL) prepared in 1× chemotaxis assay buffer is added to the lower chamber. After assembly, the plate is incubated for 2.5 hours at 37° C. under 5% carbon dioxide. Following the incubation, 5 µL of cell proliferation solution is added into the lower chamber. The plate is then incubated for 60 minutes at 37° C., and the migrated cells are detected by measuring the absorbance at 492 nm with a microplate reader. CXCR4 antagonists inhibit cell migration, reducing the absorbance reading. The inhibitory potency ($IC_{50}$) of a test antibody in this assay is calculated using GraphPad Prism software, based on the dose-dependent decrease of absorbance at 492 nm.

Antibodies exemplified herein exhibit an average IC50 value of 30 nM or less in this assay. The antibody III exhibits an average IC50 value of 5.90 nM in this assay. The data demonstrate that antibodies exemplified herein bind to human CXCR4 with high affinity and inhibit human CXCR4 binding to SDF-1.

Evaluation of Binding Activities of Anti-CXCR4 Antibodies by Surface Plasmon Resonance (BIAcore)

A Biacore® 2000 instrument is used to measure binding kinetics and affinity. The Biacore® utilizes the optical properties of surface plasmon resonance to detect alteration in protein concentration of interacting molecules within a dextran biosensor matrix. Except as noted, all reagents and materials are purchased from Biacore® AB (Upsala, Sweden). All measurements are performed at 4° C. The binding experiment is performed essentially as described in Stenlund et al (Stenlund P, Babcock G J, Sodroski J, Myszka D G. (2003) Capture and reconstitution of G protein-coupled receptors on a biosensor surface. Anal Biochem. 316(2):243-50) and Navratilo et al (Navratilova I, Sodroski J, Myszka D G. (2005) Solubilization, stabilization, and purification of chemokine receptors using biosensor technology. Anal Biochem. 339(2):271-81). Running buffer is 50 mM HEPES, 5 mM magnesium chloride, 1 mM calcium chloride, 150 mM sodium chloride, 2 mg/mL BSA, pH 7.5. The human CXCR4 receptor with a C-terminal linear C9 peptide tag (SEQ ID NO: 29), is cloned and overexpressed in canine thymocyte Cf2Th cells in the same manner as described previously by Mirzabekov et al (Mirzabekov, N. Bannert, M. Farzan, W. Hofmann, P. Kolchinsky, L. Wu, R. Wyatt and J. Sodroski—Enhanced expression, native purification, and characterization of CCR5, a principal HIV-1 coreceptor. J. Biol. Chem. 274 (1999), pp. 28745-28750). The C-terminal linear C9 peptide tag is recognized by the 1D4 monoclonal antibody (D. D. Oprian, R. S. Molday, R. J. Kaufman and H. G. Khorana, Expression of a synthetic bovine rhodopsin gene in monkey kidney cells. Proc. Natl. Acad. Sci. USA 84 (1987), pp. 8874-8878).

Binding is evaluated using multiple analytical cycles as follows. 1D4 Mab (Monoclonal clone 1D4, University of British Columbia) is immobilized to a CM5 chip via amine coupling (about 10,000-20,000 Resonance Units antibody). Cells are resuspended in 20 mM tris(hydroxymethyl)aminomethane (pH 7.0), 0.1 M ammonium sulphate, 10% glycerol, 5 mM magnesium chloride, 1 mM calcium chloride, plus complete ethylenediaminetetraacetic acid-free protease inhibitor tablet. 4×10$^6$ cells/mL final for injection onto the chip (i.e. 2.0×10$^6$ cells, 0.5 mL final volume) are used. Transfected cells and running buffer with detergent (2% cholesteryl hemisuccinate ester, 10% dodecyl maltoside, 10% 3-[(3-Cholamidopropyl)dimethylammonio]-1-propanesulfonate) at a ratio of 5:1 (cells to buffer volume ratio) are transferred into an auto-mixer. This mixture is incubated for 10 minutes. After incubation 150 µL solubilized receptor is injected over 1D4 surface at a flow rate of 20 µL/minute. The sample loop is then washed with running buffer. This is followed by an injection of 20 µL of antibody at flow rate of 100 µL/minute. The chip is then regenerated with two 10 second pulses of 10 mM sodium hydroxide+1% n-octyl-β-D-glucopyranoside at 100 µL/minute. Association rate constants ("$k_{on}$") and dissociation rate constants ("$k_{off}$") for each cycle are evaluated using a "1:1 with mass transfer" binding model in the BIAevaluation software. "$K_D$" is the dissociation constant and it is calculated by the formula: $k_{off}/k_{on}=K_D$. The binding parameters are summarized below. The data demonstrate that antibodies exemplified herein bind to human CXCR4 with high affinity and inhibit human CXCR4 binding to SDF-1.

| Antibody | $K_{on}$ (M$^{-1}$s$^{-1}$) | $K_{off}$ (s$^{-1}$) | $K_D$ (nM) |
|---|---|---|---|
| I | $2.36 \times 10^6$ | $1.61 \times 10^{-3}$ | 0.68 |
| II | $2.50 \times 10^6$ | $1.81 \times 10^{-3}$ | 0.72 |
| III | $1.12 \times 10^6$ | $1.72 \times 10^{-3}$ | 1.54 |
| IV | $7.74 \times 10^5$ | $3.98 \times 10^{-3}$ | 5.14 |
| V | $1.91 \times 10^6$ | $1.68 \times 10^{-3}$ | 0.88 |

Anti-Tumor Activity in a SCID/Namalwa Xenograft Model

SDF-1/CXCR4 interaction appears to play an important role in multiple stages of tumorigenesis, including tumor growth, invasion, angiogenesis, and metastasis. To evaluate in vivo anti-tumor activity of a test antibody in cancer, a tumor xenograft model using NOD/SCID mice and human non-Hodgkin's lymphoma Namalwa cells is employed. Briefly, 200,000 Namalwa cells mixed with matrigel (1:1) are implanted subcutaneously into the rear flank of the animals. The implanted tumor cells grow as solid tumors, the dimensions of which can be continuously monitored and measured using a caliper. To determine the in vivo efficacy of a test antibody in this model, animals (10/group) are treated with different doses of test antibodies dissolved in saline or phosphate buffered saline, 48 hours post tumor cell implantation. Antibodies are dosed subcutaneously in the range of 1 μg/mouse, 10 μg/mouse, and 100 μg/mouse, and tumor volume and body weight are determined every 2 or 3 days. The studies last generally 3-4 weeks, depending on the tumor growth. The anti-tumor growth activity of a test antibody is determined by the percent reduction in tumor volume in treatment groups compared to tumor volume in control groups treated with vehicle alone.

Antibody I inhibits tumor growth in this assay when administered at 10 μg/mouse, which is approximately 0.4 mg/kg. The data demonstrate that Antibody I has tumorigenesis activity by preventing tumor growth.

SCID/Namalwa Hematological Lymphoma Model

To further investigate anti-tumor activity of CXCR4 antibody in lymphoma, a hematological lymphoma model is established by injecting 200,000 Namalwa cells into SCID mice via tail vein. Generally, the mice injected with tumor cells die in 5-6 weeks. To test efficacy of the antibody in this model, animals (10 each group) are treated with 30 μg/mouse or 100 μg/mouse of test antibody 24 hours post tumor cell injection. The antibody is dosed subcutaneously once every 4 days for 6 weeks, and the animal survival is recorded on daily basis.

Antibody I treatment groups have shown statistically significant survival benefit when compared with vehicle and isotype IgG control groups in this hematological lymphoma model.

Anti-Tumor Activity in a SCID/CEM Xenograft Model

To evaluate in vivo anti-tumor activity of a test antibody in cancer, a tumor xenograft model using NOD/SCID mice and CEM cells is employed. Briefly, $5.0 \times 10^6$ CEM cells mixed with matrigel (1:1) are implanted subcutaneously into the rear flank of the animals. The implanted tumor cells grow as solid tumors which can be continuously monitored and measured by caliper. To determine the efficacy of a test antibody in this model, animals (10 each group) are treated with 10 μg/mouse, 30 μg/mouse, or 100 μg/mouse of test antibody 24 hours post tumor cell implantation. The antibody is dosed subcutaneously once every 4 days, and the tumor volume and body weight are measured every 2 or 3 days.

A dose-dependent tumor growth inhibition is observed among Antibody I treatment groups compared with vehicle and isotype IgG control groups. Antibody I at all three doses inhibits tumor growth significantly.

Apoptosis Assay

To investigate if CXCR4 antibodies induce apoptosis, multiple tumor cell lines expressing high levels of CXCR4 are treated with test antibody. The cells are treated with different concentrations of test antibody for 2-4 days in their growth medium with 1% or 10% FBS. After treatment, cells are fixed with 3.7% formaldehyde and washed in D-PBS. Cells are permeabilized with 0.1% Triton X-100 in D-PBS, washed and blocked in D-PBS containing 1% BSA. Cells are then incubated for 1 hour with rabbit anti-activated Caspase3 polyclonal antibody (Cat#557135 BD Biosciences, NC) diluted in D-PBS with 1% BSA. Cells are washed 2 times with D-PBS then incubated for 1 hour with Alexa Fluor 488 goat anti Rabbit IgG (Invitrogen, Carlsbad, Calif.) and 200 ng/mL Hoechst 33342 (Invitrogen, Carlsbad, Calif.) diluted in D-PBS with 1% BSA. Stained plates are scanned using ArrayScan Vti (Cellomics, Pittsburgh, Pa.) and the Target Activation bioapplication is used for quantitation of fluorescent signal.

The results demonstrate that Antibody I induces nuclear fragmentation and activation of caspase 3 in multiple tumor cells including Namalwa and CEM cells. Nuclear fragmentation and caspase 3 activation are hallmarks of apoptosis. Therefore, the data demonstrate that Antibody I induces apoptosis of tumor cells when administered between 2 μg/mL and 10 μg/mL.

To further confirm that Antibody I induces apoptosis, annexin V changes are investigated by flow cytometry in Namalwa cells after treatment with test antibody or isotype IgG control. Antibody I induces a dose-dependent increase of annexin V, while isotype IgG has no effect. Furthermore, Antibody I induces apoptosis which is also observed in CEM xenograft tumors by TUNEL staining.

We claim:

1. A human engineered antibody or a binding fragment thereof, comprising a light chain and a heavy chain, wherein the light chain comprises a light chain variable region having the amino acid sequence of SEQ ID NO:16, and the heavy chain comprises a heavy chain variable region having an amino acid sequence selected from the group consisting of SEQ ID NO:11, SEQ ID NO:12, SEQ ID NO:13, SEQ ID NO:14, and SEQ ID NO:15, wherein the antibody binds to human CXCR4.

2. The antibody of claim 1, wherein the antibody comprises a heavy chain and a light chain amino acid sequence selected from the group consisting of:
   a. a heavy chain comprising the amino acid sequence of SEQ ID NO:17 and a light chain comprising the amino acid sequence of SEQ ID NO:22,
   b. a heavy chain comprising the amino acid sequence of SEQ ID NO:18 and a light chain comprising the amino acid sequence of SEQ ID NO:22,
   c. a heavy chain comprising the amino acid sequence of SEQ ID NO:19 and a light chain comprising the amino acid sequence of SEQ ID NO:22,
   d. a heavy chain comprising the amino acid sequence of SEQ ID NO:20 and a light chain comprising the amino acid sequence of SEQ ID NO:22, and
   e. a heavy chain comprising the amino acid sequence of SEQ ID NO:21 and a light chain comprising the amino acid sequence of SEQ ID NO:22.

3. A human engineered antibody or a binding fragment thereof comprising two light chains of SEQ ID NO: 22, and two heavy chains of SEQ ID NO: 17.

4. A human engineered antibody or a binding fragment thereof comprising two light chains of SEQ ID NO: 22, and two heavy chains of SEQ ID NO: 19.

5. A pharmaceutical composition comprising the antibody of claim 1 in combination with one or more pharmaceutically acceptable carriers, diluents, or excipients.

6. A method of treating a cancer selected from the group consisting of non-Hodgkin's lymphoma and leukemia, comprising administering to a patient in need thereof a therapeutically effective amount of the antibody of claim 1.

7. A pharmaceutical composition comprising the antibody of claim 3 in combination with one or more pharmaceutically acceptable carriers, diluents, or excipients.

8. A method of treating a cancer selected from the group consisting of non-Hodgkin's lymphoma and leukemia, comprising administering to a patient in need thereof a therapeutically effective amount of the antibody of claim 3.

9. A pharmaceutical composition comprising the antibody of claim 4 in combination with one or more pharmaceutically acceptable carriers, diluents, or excipients.

10. A method of treating a cancer selected from the group consisting of non-Hodgkin's lymphoma and leukemia, comprising administering to a patient in need thereof a therapeutically effective amount of the antibody of claim 4.

* * * * *

SEQUENCE LISTING

<160> NUMBER OF SEQ ID NOS: 33

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

```
Gly Phe Thr Ser Thr Asp Tyr Tyr Phe Ser
1               5                   10

<210> SEQ ID NO 2
<211> LENGTH: 19
<212> TYPE: PRT
<213> ORGANISM: Artificial Sequence
<220> FEATURE:
<223> OTHER INFORMATION: Synthetic Construct

<400> SEQUENCE: 2

Phe Ile Arg Thr Lys Ser Lys Gly Tyr Thr Thr Glu Tyr Ser Gly Ser
1               5                   10                  15

Val Lys Gly

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Glu Pro Ile Thr Thr Asp Pro Arg Asp Tyr
1               5                   10

<210> SEQ ID NO 4
<211> LENGTH: 19
<212> TYPE: PRT
<213> ORGANISM: Artificial Sequence
<220> FEATURE:
<223> OTHER INFORMATION: Synthetic Construct

<400> SEQUENCE: 4

Phe Ile Arg Ser Lys Ser Lys Gly Tyr Thr Thr Glu Tyr Ser Gly Ser
1               5                   10                  15

Val Lys Gly

<210> SEQ ID NO 5
<211> LENGTH: 19
<212> TYPE: PRT
<213> ORGANISM: Artificial Sequence
<220> FEATURE:
<223> OTHER INFORMATION: Synthetic Construct

<400> SEQUENCE: 5

Phe Ile Arg Tyr Lys Ser Lys Gly Tyr Thr Thr Glu Tyr Ser Gly Ser
1               5                   10                  15

Val Lys Gly

<210> SEQ ID NO 6
<211> LENGTH: 19
<212> TYPE: PRT
<213> ORGANISM: Artificial Sequence
<220> FEATURE:
<223> OTHER INFORMATION: Synthetic Construct

<400> SEQUENCE: 6

Phe Ile Arg Asn Lys Arg Lys Gly Tyr Thr Thr Glu Tyr Ser Gly Ser
1               5                   10                  15

Val Lys Gly

<210> SEQ ID NO 7
```

<211> LENGTH: 19
<212> TYPE: PRT
<213> ORGANISM: Artificial Sequence
<220> FEATURE:
<223> OTHER INFORMATION: Synthetic Construct

<400> SEQUENCE: 7

```
Phe Ile Arg His Lys Ser Lys Gly Tyr Thr Thr Glu Tyr Ser Gly Ser
1               5                   10                  15

Val Lys Gly
```

<210> SEQ ID NO 8
<211> LENGTH: 17
<212> TYPE: PRT
<213> ORGANISM: Artificial Sequence
<220> FEATURE:
<223> OTHER INFORMATION: Synthetic Construct

<400> SEQUENCE: 8

```
Lys Ser Ser Gln Ser Leu Phe Asn Ser Arg Thr Arg Lys Lys Tyr Leu
1               5                   10                  15

Ala
```

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

```
Trp Ala Ser Lys Arg Lys Ser
1               5
```

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

```
Lys Gln Ser Arg Phe Leu Arg Ala
1               5
```

<210> SEQ ID NO 11
<211> LENGTH: 121
<212> TYPE: PRT
<213> ORGANISM: Artificial Sequence
<220> FEATURE:
<223> OTHER INFORMATION: Synthetic Construct

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Thr Asp Tyr
            20                  25                  30

Tyr Phe Ser Trp Val Arg Gln Ala Pro Gly Lys Gly Leu Glu Trp Val
        35                  40                  45

Gly Phe Ile Arg Thr Lys Ser Lys Gly Tyr Thr Thr Glu Tyr Ser Gly
    50                  55                  60

Ser Val Lys Gly Arg Phe Thr Ile Ser Arg Asp Asp Ser Lys Asn Ser
65                  70                  75                  80
```

```
Leu Tyr Leu Gln Met Asn Ser Leu Lys Thr Glu Asp Thr Ala Val Tyr
                85                  90                  95

Tyr Cys Ala Arg Glu Pro Ile Thr Thr Asp Pro Arg Asp Tyr Trp Gly
            100                 105                 110

Gln Gly Thr Leu Val Thr Val Ser Ser
        115                 120

<210> SEQ ID NO 12
<211> LENGTH: 121
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Thr Asp Tyr
            20                  25                  30

Tyr Phe Ser Trp Val Arg Gln Ala Pro Gly Lys Gly Leu Glu Trp Val
        35                  40                  45

Gly Phe Ile Arg Ser Lys Ser Lys Gly Tyr Thr Thr Glu Tyr Ser Gly
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Ile Thr Thr Asp Pro Arg Asp Tyr Trp Gly
            100                 105                 110

Gln Gly Thr Leu Val Thr Val Ser Ser
        115                 120

<210> SEQ ID NO 13
<211> LENGTH: 121
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Thr Asp Tyr
            20                  25                  30

Tyr Phe Ser Trp Val Arg Gln Ala Pro Gly Lys Gly Leu Glu Trp Val
        35                  40                  45

Gly Phe Ile Arg Tyr Lys Ser Lys Gly Tyr Thr Thr Glu Tyr Ser Gly
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Ile Thr Thr Asp Pro Arg Asp Tyr Trp Gly
            100                 105                 110

Gln Gly Thr Leu Val Thr Val Ser Ser
        115                 120

<210> SEQ ID NO 14
```

```
<211> LENGTH: 121
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Thr Asp Tyr
            20                  25                  30

Tyr Phe Ser Trp Val Arg Gln Ala Pro Gly Lys Gly Leu Glu Trp Val
        35                  40                  45

Gly Phe Ile Arg Asn Lys Arg Lys Gly Tyr Thr Thr Glu Tyr Ser Gly
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Ile Thr Thr Asp Pro Arg Asp Tyr Trp Gly
            100                 105                 110

Gln Gly Thr Leu Val Thr Val Ser Ser
        115                 120

<210> SEQ ID NO 15
<211> LENGTH: 121
<212> TYPE: PRT
<213> ORGANISM: Artificial Sequence
<220> FEATURE:
<223> OTHER INFORMATION: Synthetic Construct

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Thr Asp Tyr
            20                  25                  30

Tyr Phe Ser Trp Val Arg Gln Ala Pro Gly Lys Gly Leu Glu Trp Val
        35                  40                  45

Gly Phe Ile Arg His Lys Ser Lys Gly Tyr Thr Thr Glu Tyr Ser Gly
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Ile Thr Thr Asp Pro Arg Asp Tyr Trp Gly
            100                 105                 110

Gln Gly Thr Leu Val Thr Val Ser Ser
        115                 120

<210> SEQ ID NO 16
<211> LENGTH: 112
<212> TYPE: PRT
<213> ORGANISM: Artificial Sequence
<220> FEATURE:
<223> OTHER INFORMATION: Synthetic Construct

<400> SEQUENCE: 16

Asp Ile Val Met Thr Gln Ser Pro Asp Ser Leu Ala Val Ser Leu Gly
1               5                   10                  15
```

```
Glu Arg Ala Thr Ile Asn Cys Lys Ser Ser Gln Ser Leu Phe Asn Ser
                 20                  25                  30

Arg Thr Arg Lys Lys Tyr Leu Ala Trp Tyr Gln Gln Lys Pro Gly Gln
             35                  40                  45

Pro Pro Lys Leu Leu Ile Tyr Trp Ala Ser Lys Arg Lys Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95

Ser Arg Phe Leu Arg Ala Phe Gly Gln Gly Thr Lys Leu Glu Ile Lys
            100                 105                 110
```

<210> SEQ ID NO 17
<211> LENGTH: 447
<212> TYPE: PRT
<213> ORGANISM: Artificial Sequence
<220> FEATURE:
<223> OTHER INFORMATION: Synthetic Construct

<400> SEQUENCE: 17

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Ser Thr Asp Tyr
                 20                  25                  30

Tyr Phe Ser Trp Val Arg Gln Ala Pro Gly Lys Gly Leu Glu Trp Val
             35                  40                  45

Gly Phe Ile Arg Thr Lys Ser Lys Gly Tyr Thr Thr Glu Tyr Ser Gly
 50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ala Arg Glu Pro Ile Thr Thr Asp Pro Arg Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
            210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270
```

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445

<210> SEQ ID NO 18
<211> LENGTH: 447
<212> TYPE: PRT
<213> ORGANISM: Artificial Sequence
<220> FEATURE:
<223> OTHER INFORMATION: Synthetic Construct

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Thr Asp Tyr
            20                  25                  30

Tyr Phe Ser Trp Val Arg Gln Ala Pro Gly Lys Gly Leu Glu Trp Val
        35                  40                  45

Gly Phe Ile Arg Ser Lys Ser Lys Gly Tyr Thr Thr Glu Tyr Ser Gly
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Ile Thr Thr Asp Pro Arg Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

```
Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
        260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
        340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly
        435                 440                 445

<210> SEQ ID NO 19
<211> LENGTH: 447
<212> TYPE: PRT
<213> ORGANISM: Artificial Sequence
<220> FEATURE:
<223> OTHER INFORMATION: Synthetic Construct

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Thr Asp Tyr
            20                  25                  30

Tyr Phe Ser Trp Val Arg Gln Ala Pro Gly Lys Gly Leu Glu Trp Val
        35                  40                  45

Gly Phe Ile Arg Tyr Lys Ser Lys Gly Tyr Thr Thr Glu Tyr Ser Gly
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Ile Thr Thr Asp Pro Arg Asp Tyr Trp Gly
            100                 105                 110
```

```
Gln Gly Thr Leu Val Thr Val Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445

<210> SEQ ID NO 20
<211> LENGTH: 447
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Thr Asp Tyr
            20                  25                  30
```

-continued

```
Tyr Phe Ser Trp Val Arg Gln Ala Pro Gly Lys Gly Leu Glu Trp Val
         35                  40                  45

Gly Phe Ile Arg Asn Lys Arg Lys Gly Tyr Thr Thr Glu Tyr Ser Gly
         50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ala Arg Glu Pro Ile Thr Thr Asp Pro Arg Asp Tyr Trp Gly
                100                 105                 110

Gln Gly Thr Leu Val Thr Val Ser Ala Ser Thr Lys Gly Pro Ser
                115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
                195                 200                 205

Lys Pro Ser Asn Thr Lys Val Asp Lys Arg Val Glu Ser Lys Tyr Gly
        210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly
        435                 440                 445
```

<210> SEQ ID NO 21
<211> LENGTH: 447
<212> TYPE: PRT
<213> ORGANISM: Artificial Sequence
<220> FEATURE:
<223> OTHER INFORMATION: Synthetic Construct

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Thr Asp Tyr
            20                  25                  30

Tyr Phe Ser Trp Val Arg Gln Ala Pro Gly Lys Gly Leu Glu Trp Val
        35                  40                  45

Gly Phe Ile Arg His Lys Ser Lys Gly Tyr Thr Thr Glu Tyr Ser Gly
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Ile Thr Thr Asp Pro Arg Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
                150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Lys Thr Tyr Thr Cys Asn Val Asp His
    195                 200                 205

Lys Pro Ser Asn Thr Lys Val Asp Lys Arg Val Glu Ser Lys Tyr Gly
210                 215                 220                 225

Pro Pro Cys Pro Pro Cys Pro Ala Pro Glu Ala Ala Gly Gly Pro Ser
                230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
        260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Tyr Arg Val Val
290                 295                 300                 305

Ser Val Leu Thr Val Leu His Gln Asp Trp Leu Asn Gly Lys Glu Tyr
                310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Gln Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
```

```
                370             375             380             385
Asn Gly Gln Pro Glu Asn Asn Tyr Lys Thr Thr Pro Pro Val Leu Asp
            390                 395                 400
Ser Asp Gly Ser Phe Phe Leu Tyr Ser Arg Leu Thr Val Asp Lys Ser
        405                 410                 415
Arg Trp Gln Glu Gly Asn Val Phe Ser Cys Ser Val Met His Glu Ala
    420                 425                 430
Leu His Asn His Tyr Thr Gln Lys Ser Leu Ser Leu Ser Leu Gly
435                 440                 445

<210> SEQ ID NO 22
<211> LENGTH: 219
<212> TYPE: PRT
<213> ORGANISM: Artificial Sequence
<220> FEATURE:
<223> OTHER INFORMATION: Synthetic Construct

<400> SEQUENCE: 22

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Phe Asn Ser
            20                  25                  30
Arg Thr Arg Lys Lys Tyr Leu Ala Trp Tyr Gln Gln Lys Pro Gly Gln
        35                  40                  45
Pro Pro Lys Leu Leu Ile Tyr Trp Ala Ser Lys Arg Lys Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Lys Gln
                85                  90                  95
Ser Arg Phe Leu Arg Ala Phe Gly Gln Gly Thr Lys Leu Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215

<210> SEQ ID NO 23
<211> LENGTH: 363
<212> TYPE: DNA
<213> ORGANISM: Artificial Sequence
<220> FEATURE:
<223> OTHER INFORMATION: Synthetic Construct

<400> SEQUENCE: 23
gaggtgcagc tggtggagtc tgggggaggc ttggtccagc ctggagggtc cctgagactc      60
tcctgtgcag cctctggctt caccagtacc gactactact tagctgggt ccgccaggct      120
```

```
ccagggaagg ggctggagtg ggttggcttc atccggacga agtcgaaggg ctacaccacc      180
gagtacagcg gcagcgtgaa gggcagattc accatctcaa gagatgattc aaagaactca      240
ctgtacctgc agatgaacag cctgaaaacc gaggacacgg ccgtgtatta ctgtgctaga      300
gagcccatca ccaccgaccc tcgggactac tggggccaag ggaccctggt caccgtctcc      360
tca                                                                    363

<210> SEQ ID NO 24
<211> LENGTH: 363
<212> TYPE: DNA
<213> ORGANISM: Artificial Sequence
<220> FEATURE:
<223> OTHER INFORMATION: Synthetic Construct

<400> SEQUENCE: 24
gaggtgcagc tggtggagtc tgggggaggc ttggtccagc ctggagggtc cctgagactc       60
tcctgtgcag cctctggctt caccagtacc gactactact ttagctgggt ccgccaggct      120
ccagggaagg ggctggagtg ggttggcttc atccggtcta agtcgaaggg ctacaccacc      180
gagtacagcg gcagcgtgaa gggcagattc accatctcaa gagatgattc aaagaactca      240
ctgtacctgc agatgaacag cctgaaaacc gaggacacgg ccgtgtatta ctgtgctaga      300
gagcccatca ccaccgaccc tcgggactac tggggccaag ggaccctggt caccgtctcc      360
tca                                                                    363

<210> SEQ ID NO 25
<211> LENGTH: 363
<212> TYPE: DNA
<213> ORGANISM: Artificial Sequence
<220> FEATURE:
<223> OTHER INFORMATION: Synthetic Construct

<400> SEQUENCE: 25
gaggtgcagc tggtggagtc tgggggaggc ttggtccagc ctggagggtc cctgagactc       60
tcctgtgcag cctctggctt caccagtacc gactactact ttagctgggt ccgccaggct      120
ccagggaagg ggctggagtg ggttggcttc atccggtata agtcgaaggg ctacaccacc      180
gagtacagcg gcagcgtgaa gggcagattc accatctcaa gagatgattc aaagaactca      240
ctgtacctgc agatgaacag cctgaaaacc gaggacacgg ccgtgtatta ctgtgctaga      300
gagcccatca ccaccgaccc tcgggactac tggggccaag ggaccctggt caccgtctcc      360
tca                                                                    363

<210> SEQ ID NO 26
<211> LENGTH: 363
<212> TYPE: DNA
<213> ORGANISM: Artificial Sequence
<220> FEATURE:
<223> OTHER INFORMATION: Synthetic Construct

<400> SEQUENCE: 26
gaggtgcagc tggtggagtc tgggggaggc ttggtccagc ctggagggtc cctgagactc       60
tcctgtgcag cctctggctt caccagtacc gactactact ttagctgggt ccgccaggct      120
ccagggaagg ggctggagtg ggttggcttc atccggaaca agcggaaggg ctacaccacc      180
gagtacagcg gcagcgtgaa gggcagattc accatctcaa gagatgattc aaagaactca      240
ctgtacctgc agatgaacag cctgaaaacc gaggacacgg ccgtgtatta ctgtgctaga      300
```

-continued

| | |
|---|---|
| gagcccatca ccaccgaccc tcgggactac tggggccaag ggaccctggt caccgtctcc | 360 |
| tca | 363 |

<210> SEQ ID NO 27
<211> LENGTH: 363
<212> TYPE: DNA
<213> ORGANISM: Artificial Sequence
<220> FEATURE:
<223> OTHER INFORMATION: Synthetic Construct

<400> SEQUENCE: 27

| | |
|---|---|
| gaggtgcagc tggtggagtc tgggggaggc ttggtccagc ctggagggtc cctgagactc | 60 |
| tcctgtgcag cctctggctt caccagtacc gactactact tagctgggt ccgccaggct | 120 |
| ccagggaagg gctggagtg ggttggcttc atccggcaca agtcgaaggg ctacaccacc | 180 |
| gagtacagcg gcagcgtgaa gggcagattc accatctcaa gagatgattc aaagaactca | 240 |
| ctgtacctgc agatgaacag cctgaaaacc gaggacacgg ccgtgtatta ctgtgctaga | 300 |
| gagcccatca ccaccgaccc tcgggactac tggggccaag ggaccctggt caccgtctcc | 360 |
| tca | 363 |

<210> SEQ ID NO 28
<211> LENGTH: 336
<212> TYPE: DNA
<213> ORGANISM: Artificial Sequence
<220> FEATURE:
<223> OTHER INFORMATION: Synthetic Construct

<400> SEQUENCE: 28

| | |
|---|---|
| gacatcgtga tgacccagtc tccagactcc ctggctgtgt ctctgggcga gagggccacc | 60 |
| atcaactgca agagcagcca gagcctgttc aacagccgga cccggaagaa gtacctggcc | 120 |
| tggtaccagc agaaaccagg acagcctcct aagctgctca tttactgggc cagcaagaga | 180 |
| aagagcgggg tccctgaccg attcagtggc agcgggtctg ggacagattt cactctcacc | 240 |
| atcagcagcc tgcaggctga agatgtggca gtttattact gtaagcagag ccgttttctg | 300 |
| agagcctttg gccaagggac caagctggag atcaaa | 336 |

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct

<400> SEQUENCE: 29

Thr Glu Thr Ser Gln Val Ala Pro Ala
1               5

<210> SEQ ID NO 30
<211> LENGTH: 360
<212> TYPE: PRT
<213> ORGANISM: Homo sapiens

<400> SEQUENCE: 30

Met Glu Gly Ile Ser Ser Ile Pro Leu Pro Leu Leu Gln Ile Tyr Thr
1               5                   10                  15

Ser Asp Asn Tyr Thr Glu Glu Met Gly Ser Gly Asp Tyr Asp Ser Met
                20                  25                  30

Lys Glu Pro Cys Phe Arg Glu Glu Asn Ala Asn Phe Asn Lys Ile Phe
            35                  40                  45

Leu Pro Thr Ile Tyr Ser Ile Ile Phe Leu Thr Gly Ile Val Gly Asn
        50                  55                  60

Gly Leu Val Ile Leu Val Met Gly Tyr Gln Lys Lys Leu Arg Ser Met
 65                  70                  75                  80

Thr Asp Lys Tyr Arg Leu His Leu Ser Val Ala Asp Leu Leu Phe Val
                85                  90                  95

Ile Thr Leu Pro Phe Trp Ala Val Asp Ala Val Ala Asn Trp Tyr Phe
            100                 105                 110

Gly Asn Phe Leu Cys Lys Ala Val His Val Ile Tyr Thr Val Asn Leu
        115                 120                 125

Tyr Ser Ser Val Leu Ile Leu Ala Phe Ile Ser Leu Asp Arg Tyr Leu
    130                 135                 140

Ala Ile Val His Ala Thr Asn Ser Gln Arg Pro Arg Lys Leu Leu Ala
145                 150                 155                 160

Glu Lys Val Val Tyr Val Gly Val Trp Ile Pro Ala Leu Leu Leu Thr
                165                 170                 175

Ile Pro Asp Phe Ile Phe Ala Asn Val Ser Glu Ala Asp Asp Arg Tyr
            180                 185                 190

Ile Cys Asp Arg Phe Tyr Pro Asn Asp Leu Trp Val Val Phe Gln
        195                 200                 205

Phe Gln His Ile Met Val Gly Leu Ile Leu Pro Gly Ile Val Ile Leu
    210                 215                 220

Ser Cys Tyr Cys Ile Ile Ile Ser Lys Leu Ser His Ser Lys Gly His
225                 230                 235                 240

Gln Lys Arg Lys Ala Leu Lys Thr Thr Val Ile Leu Ile Leu Ala Phe
                245                 250                 255

Phe Ala Cys Trp Leu Pro Tyr Tyr Ile Gly Ile Ser Ile Asp Ser Phe
            260                 265                 270

Ile Leu Leu Glu Ile Ile Lys Gln Gly Cys Glu Phe Glu Asn Thr Val
        275                 280                 285

His Lys Trp Ile Ser Ile Thr Glu Ala Leu Ala Phe Phe His Cys Cys
    290                 295                 300

Leu Asn Pro Ile Leu Tyr Ala Phe Leu Gly Ala Lys Phe Lys Thr Ser
305                 310                 315                 320

Ala Gln His Ala Leu Thr Ser Val Ser Arg Gly Ser Ser Leu Lys Ile
                325                 330                 335

Leu Ser Lys Gly Lys Arg Gly Gly His Ser Ser Val Ser Thr Glu Ser
            340                 345                 350

Glu Ser Ser Ser Phe His Ser Ser
        355                 360

<210> SEQ ID NO 31
<211> LENGTH: 356
<212> TYPE: PRT
<213> ORGANISM: Homo sapiens

<400> SEQUENCE: 31

Met Ser Ile Pro Leu Pro Leu Leu Gln Ile Tyr Thr Ser Asp Asn Tyr
 1               5                  10                  15

Thr Glu Glu Met Gly Ser Gly Asp Tyr Asp Ser Met Lys Glu Pro Cys
                20                  25                  30

Phe Arg Glu Glu Asn Ala Asn Phe Asn Lys Ile Phe Leu Pro Thr Ile
            35                  40                  45

Tyr Ser Ile Ile Phe Leu Thr Gly Ile Val Gly Asn Gly Leu Val Ile

```
                 50                  55                  60
Leu Val Met Gly Tyr Gln Lys Lys Leu Arg Ser Met Thr Asp Lys Tyr
 65                  70                  75                  80

Arg Leu His Leu Ser Val Ala Asp Leu Phe Val Ile Thr Leu Pro
                 85                  90                  95

Phe Trp Ala Val Asp Ala Val Ala Asn Trp Tyr Phe Gly Asn Phe Leu
                100                 105                 110

Cys Lys Ala Val His Val Ile Tyr Thr Val Asn Leu Tyr Ser Ser Val
                115                 120                 125

Leu Ile Leu Ala Phe Ile Ser Leu Asp Arg Tyr Leu Ala Ile Val His
130                 135                 140

Ala Thr Asn Ser Gln Arg Pro Arg Lys Leu Leu Ala Glu Lys Val Val
145                 150                 155                 160

Tyr Val Gly Val Trp Ile Pro Ala Leu Leu Leu Thr Ile Pro Asp Phe
                165                 170                 175

Ile Phe Ala Asn Val Ser Glu Ala Asp Asp Arg Tyr Ile Cys Asp Arg
                180                 185                 190

Phe Tyr Pro Asn Asp Leu Trp Val Val Val Phe Gln Phe Gln His Ile
                195                 200                 205

Met Val Gly Leu Ile Leu Pro Gly Ile Val Ile Leu Ser Cys Tyr Cys
210                 215                 220

Ile Ile Ile Ser Lys Leu Ser His Ser Lys Gly His Gln Lys Arg Lys
225                 230                 235                 240

Ala Leu Lys Thr Thr Val Ile Leu Ile Leu Ala Phe Phe Ala Cys Trp
                245                 250                 255

Leu Pro Tyr Tyr Ile Gly Ile Ser Ile Asp Ser Phe Ile Leu Leu Glu
                260                 265                 270

Ile Ile Lys Gln Gly Cys Glu Phe Glu Asn Thr Val His Lys Trp Ile
                275                 280                 285

Ser Ile Thr Glu Ala Leu Ala Phe Phe His Cys Cys Leu Asn Pro Ile
290                 295                 300

Leu Tyr Ala Phe Leu Gly Ala Lys Phe Lys Thr Ser Ala Gln His Ala
305                 310                 315                 320

Leu Thr Ser Val Ser Arg Gly Ser Ser Leu Lys Ile Leu Ser Lys Gly
                325                 330                 335

Lys Arg Gly Gly His Ser Ser Val Ser Thr Glu Ser Glu Ser Ser Ser
                340                 345                 350

Phe His Ser Ser
        355

<210> SEQ ID NO 32
<211> LENGTH: 352
<212> TYPE: PRT
<213> ORGANISM: Homo sapiens

<400> SEQUENCE: 32

Met Glu Gly Ile Ser Ile Tyr Thr Ser Asp Asn Tyr Thr Glu Glu Met
 1                   5                  10                  15

Gly Ser Gly Asp Tyr Asp Ser Met Lys Glu Pro Cys Phe Arg Glu Glu
                 20                  25                  30

Asn Ala Asn Phe Asn Lys Ile Phe Leu Pro Thr Ile Tyr Ser Ile Ile
                 35                  40                  45

Phe Leu Thr Gly Ile Val Gly Asn Gly Leu Val Ile Leu Val Met Gly
                 50                  55                  60
```

```
Tyr Gln Lys Lys Leu Arg Ser Met Thr Asp Lys Tyr Arg Leu His Leu
 65                  70                  75                  80

Ser Val Ala Asp Leu Leu Phe Val Ile Thr Leu Pro Phe Trp Ala Val
                 85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
        130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
        195                 200                 205

Ile Leu Pro Gly Ile Val Ile Leu Ser Cys Tyr Cys Ile Ile Ile Ser
210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350

<210> SEQ ID NO 33
<211> LENGTH: 67
<212> TYPE: PRT
<213> ORGANISM: Homo sapiens

<400> SEQUENCE: 33

Lys Pro Val Ser Leu Ser Tyr Arg Cys Pro Cys Arg Phe Phe Glu Ser
  1               5                  10                  15

His Val Ala Arg Ala Asn Val Lys His Leu Lys Ile Leu Asn Thr Pro
                 20                  25                  30

Asn Cys Ala Leu Gln Ile Val Ala Arg Leu Asn Asn Asn Arg Gln Val
             35                  40                  45

Cys Ile Asp Pro Lys Leu Lys Trp Ile Gln Glu Tyr Leu Glu Lys Ala
         50                  55                  60

Leu Asn Lys
 65
```